United States Patent [19]

Doan

[11] Patent Number: 5,545,203

[45] Date of Patent: Aug. 13, 1996

[54] CRUSH RESISTANT MULTI-CONDUCTOR LEAD BODY

[75] Inventor: Phong D. Doan, Stevenson Ranch, Calif.

[73] Assignee: Pacesetter, Inc., Sylmar, Calif.

[21] Appl. No.: 390,321

[22] Filed: Feb. 16, 1995

Related U.S. Application Data

[63] Continuation-in-part of Ser. No. 54,571, Apr. 27, 1993, Pat. No. 5,466,253.

[51] Int. Cl.$^6$ ............................................. A61N 1/05
[52] U.S. Cl. ................................................ 607/122
[58] Field of Search ................................ 607/122, 123, 607/119

[56] References Cited

U.S. PATENT DOCUMENTS

| | | | |
|---|---|---|---|
| 5,016,646 | 5/1991 | Gotthardt et al. | 607/122 |
| 5,044,375 | 9/1991 | Bach, Jr. et al. | 607/122 |

*Primary Examiner*—William E. Kamm
*Assistant Examiner*—Scott M. Getzow
*Attorney, Agent, or Firm*—Harold C. Schloss

[57] ABSTRACT

An implantable pacing lead having a flexible insulative material injected into the passageway accommodating the electrical conductor(s) to encapsulate the conductor(s) for at least the portion of the lead body most subject to physical damage to in the lead body.

24 Claims, 3 Drawing Sheets

CRUSH RESISTANT MULTI-CONDUCTOR LEAD BODY

This is a continuation-in-part of application Ser. No. 08/054,571, filed Apr. 27, 1993 now U.S. Pat. No. 5,466,253.

BACKGROUND OF THE INVENTION

This invention relates generally to an implantable pacing lead for use with a cardiac pacemaker, and more specifically, to a pacing lead having lead body wherein the conductors are protected from being crushed by the subclavian bone and muscle structure.

Clinical evidence suggests that certain upper extremity activities are contraindicated for persons with permanent pacemakers because they require movements that can cause damage to leads. Currently, leads used in cardiac stimulation are often implanted transvenously or transthoracically with the result that the lead body can be physically crushed by either bones (i.e. "first rib-clavicle") or by tissue (costoclavicular ligament complex, subclavius muscle) and by anchoring sleeves which are tied-down so tightly that the lead body can be crushed or damaged. The result of these crushing or constrictive stresses can be severe damage to the conductors within the lead body which, in turn, can result in failed conductors and/or failed insulation.

Some leads and central venous catheters placed by percutaneous subclavian venipuncture have developed a number or problems that are apparently associated with the costoclavicular region near the superior thoracic aperture. Catheters or leads implanted by subclavian venipuncture can be damaged by bony compression or impingement by dense tissues as the lead passes through the vein beneath the clavicle, over the first rib, and into the thorax just lateral to the sternoclavicular joint. Studies suggest that an overriding clavicle can crush leads against the first rib with a "pincher-like" action. Leads can also be compressed within the costoclavicular ligament complex.

Conductor mechanical damage including fractures and/or insulation breaks occurs in about 2% to 3% of all implanted leads. In patients who are not pacemaker dependent, the event is usually not life-threatening, but can require invasive corrective procedures with potential complications. Mechanical damage is defined as coil deformation, coil fracture, mechanically induced insulation breeches, and insulation wear observed individually or in combination. Pacing lead coils under compression are characterized by flattened helical conductors. Fatigue fractures resulting from repeated cyclic compressive loading usually initiate at the outer surface of the coil.

A recent study, by Donald M. Jacobs et al., published in Part I of the March 1993 issue of *Pace Magazine*, documents the mechanisms involved in the compression deformation of implanted leads. The study involved 49 compression damaged leads of one manufacturer. While the study was aimed at identifying causes of lead compression and different implant techniques that avoid causing compression damage to the lead, they identified the site of the damage as being 27.5+/-5.2 centimeters distal to the connector pin on 58 centimeter leads.

In view of the foregoing, it has been proposed that the percutaneous subclavian venipuncture approach should be abandoned because the incidence of lead fracture in the costoclavicular region is unacceptable. However, it is also recognized that this method of implant has become the standard procedure for the majority of pacemaker lead implants. Accordingly, it would be beneficial to have a lead design which resists rib-clavicle, tissue and suture sleeve imposed mechanical damage, and allows continuation of accepted implanting procedures.

SUMMARY OF THE INVENTION

The present invention is applicable to leads having single or multiple coaxial conductors which are helically wound, as well as for multilumen tubing leads. More specifically, conductors which are confined within and/or separated by two coaxial cylindrical tubings, are coated and encapsulated in a flexible insulative protective material, which minimizes the physical stresses noted above, preventing damage to the conductors and insulation tubing in the lead body. The portion of the lead which includes the protective material is in the area subject to compression.

Alternatively, the pacing lead can be formed using a multilumen tube, which is generally an elongated length of silicone tubing having multiple axially aligned channels or lumens extending therethrough. When the multilumen tubing is assembled with other components of the system, the individual conductors are inserted into the lumens of the multilumen tubing, and advanced to their point of interconnection to their respective electrodes at the distal end and electrical connectors at the proximal end. The conductors within the lumens are coated and encapsulated with the flexible insulative protective material.

DETAILED DESCRIPTION

Figure 1:
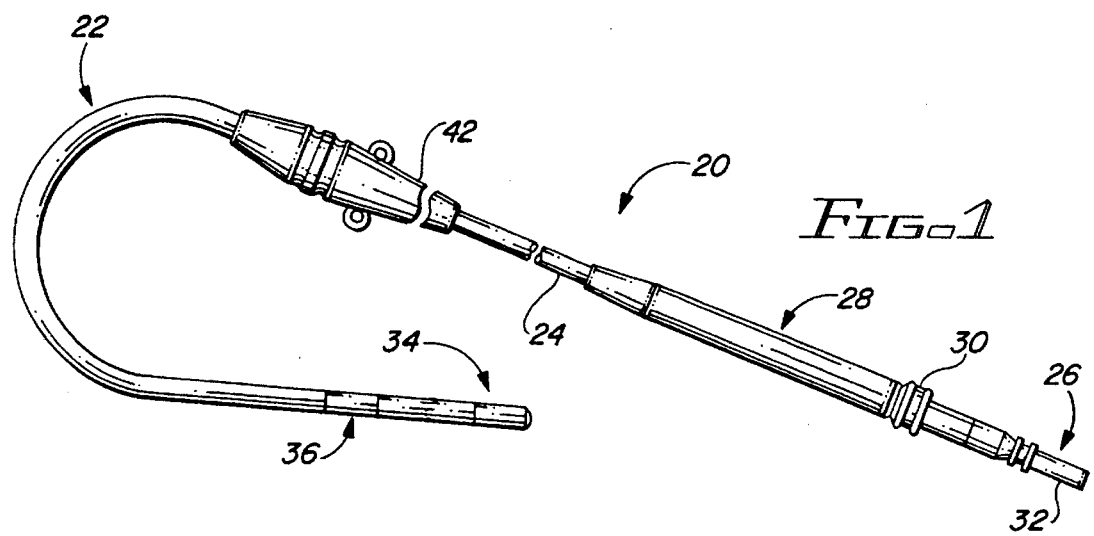
FIG. 1 shows a plan view of a pacing lead of the present invention.

FIG. 1 shows a pacing lead 20. The pacing lead 20 is provided with an elongated lead body 22 which includes a pair of coaxially mounted, helically wound electrical conductors covered with an insulation sheath 24. The sheath 24 is preferably fabricated of silicone rubber, polyurethane or other suitable plastic tubing.

At a proximal end 26 of the pacing lead 20 is a connector assembly 28, which is provided with sealing rings 30 and which carries at least one electrical connector 32. The connector assembly 28 is constructed using known techniques and is preferably fabricated of silicone rubber, polyurethane or other suitable plastic. The electrical connectors 32 are preferably fabricated of stainless steel or other suitable conductive material. At a distal end 34 of the pacing lead 20 is an electrode assembly 36, which may include multiple electrodes or sensors, and which is intended to be implanted into the heart.

Figure 2:
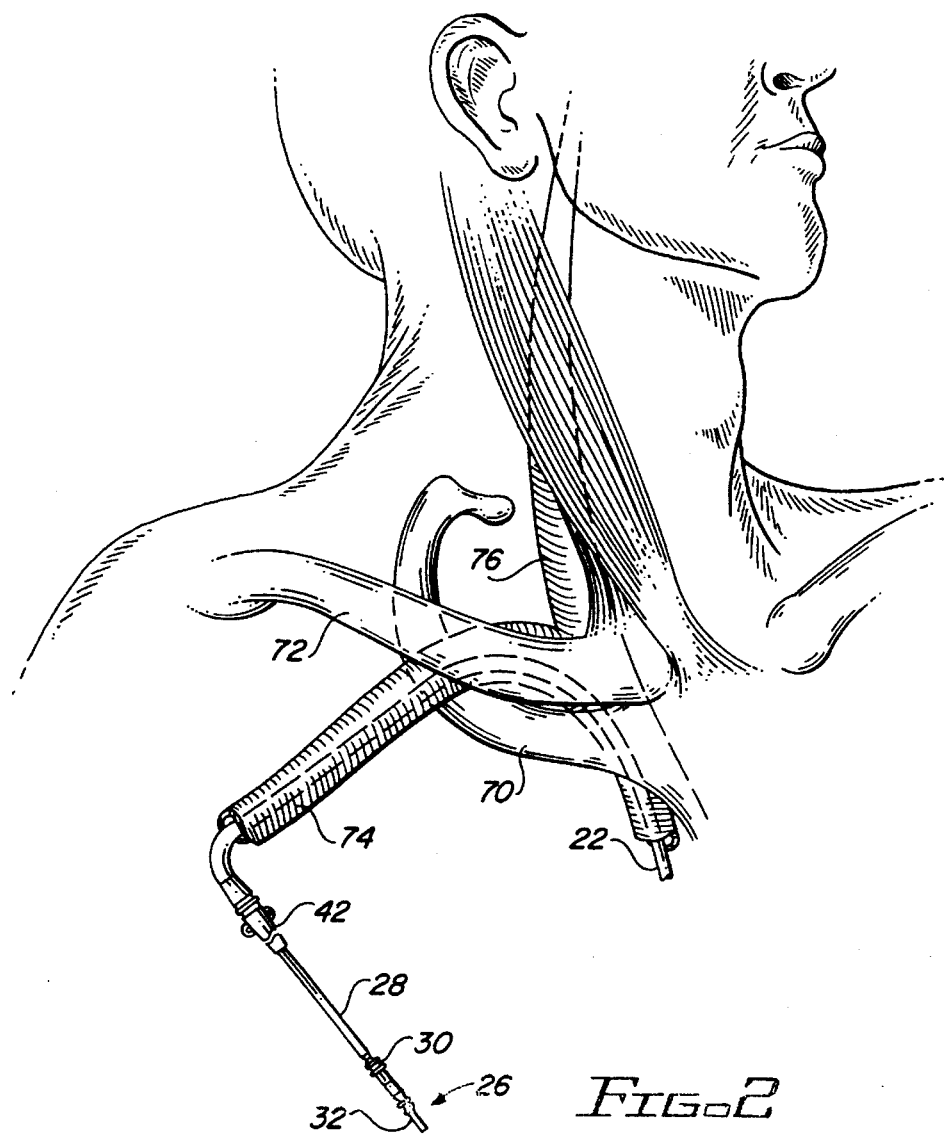
FIG. 2 shows a partially schematic view of the implanted pacing lead in the area of venous insertion, and the proximate skeletal structure.

FIG. 2 illustrates the right side neck-shoulder area of a patient. In FIG. 2, the first rib 70 and right clavicle 72 of the skeletal structure are illustrated. The subclavian vein 74 passes between the first rib 70 and right clavicle 72 before merging with the internal jugular vein 76 and proceeding to the heart (not shown). The pacing lead 20 is inserted into the subclavian vein 74, and extends through the rib 70—clavicle 72 crossing point and down the jugular vein to the heart (not shown). A fixation sleeve 42, which may be either fixed or slidably mounted around lead body 22, serves to stabilize the pacing lead 20 at the site of venous insertion.

Figure 3:
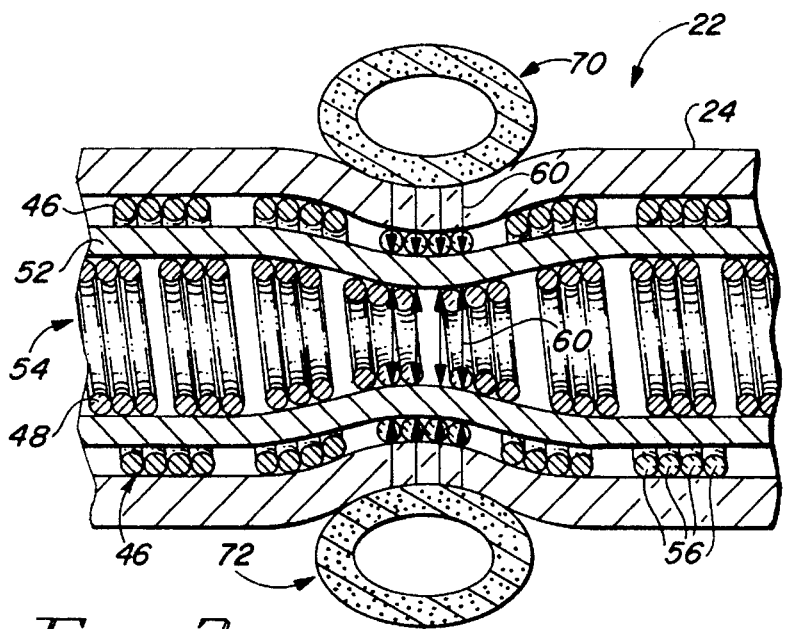
FIG. 3 shows a detailed cutaway axial view of a pacing lead in the area of the subclavian transition.
Figure 4:
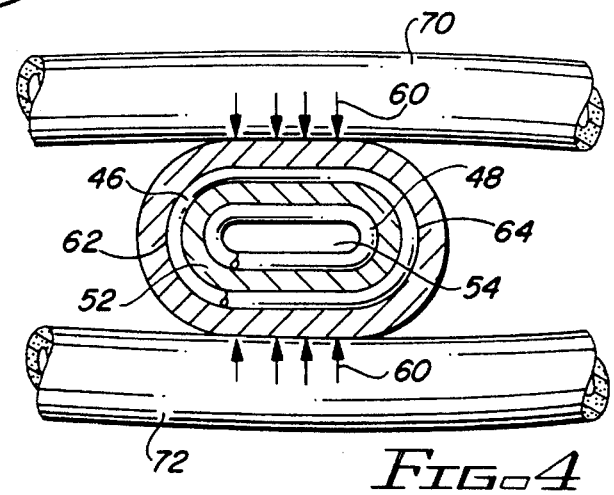
FIG. 4 shows a cross-sectional view of the pacing lead in the area of the subclavian transition.

An enlarged cross-sectional view of a portion of a pacing lead of the prior art in the area of the rib 70—clavicle 72 crossing point is illustrated in the axial view of FIG. 3 and the cross-sectional view of FIG. 4. The lead body includes two conductors 46, 48, separated by insulation tubing 52, all contained within the insulation sheath 24. The spiral winding of the conductor(s) 46, 48 results in a hollow central area 54, and allows the lead body 22 to remain quite flexible. Also, the hollow central area 54 accommodates insertion of a guide wire or stylet (not shown) which is relatively stiff and which allows the doctor to guide and control the implantation of the pacing lead 20.

The axial view in FIG. 3 of the lead body 22, in the area traversing between the first rib 70 and clavicle 72, illustrates the problem addressed by the present invention. In FIG. 3, the outer conductor 46 is illustrated as being contained between the insulation sheath 24 on the outside and an insulation tubing 52 at its inner diameter. The conductor 46, as discussed above, is a helically wound conductor, and therefore the axial view depicts cross-sections of the conductor 46. In addition, it should be understood that the conductor 46 may be made up of a plurality of conductors contained in a bundle 56 to provide redundancy while also retaining flexibility by reducing the cross-sectional thickness which would be required for a single conductor. In addition, the second conductor 48 which is also helically wound is disposed internally of the insulation tubing 52.

The hollow central area must be maintained in order to allow insertion of the stylet to guide implantation. Accordingly, the lead body illustrated in FIGS. 3 and 4 is subject to crushing by the first rib 70 and clavicle 72 during various activities performed by the recipient of the pacing system. The structural forces exerted on the conductor 46, as well as the insulation tubing 52, are identified by the arrows 60. It must also be recognized that the cylindrical structure of the lead body 22 will require that the constriction caused by the first rib 70 and clavicle 72 illustrated in FIG. 2 will cause flattening of the lead body 22, which results in sharp bending deformation of the coil conductors 46 and 48, as illustrated in the cross-sectional view of FIG. 4 at locations 62 and 64.

As has been shown, the deformation of the lead occurs typically 27.5 centimeters distal to the connector pin for 58 centimeter leads implanted in the right ventricle. By simple subtraction we can see that this spot is located 30.5 centimeters proximal to the distal tip of the lead. Allowing for the entire 10.4 centimeter range of points where damage may occur, we can see that the area of protection is portion of the lead extending from 25.3 centimeters to 35.7 centimeters proximal to the distal tip of the lead.

Pacemakers lead come in various lengths. Some pacemaker leads can be as long as 100 centimeters or so in length. The 10.4 centimeter portion of the lead that is preferably protected from crushing would in this instance be about 10 percent of the total length of the lead. So in terms of the percentage of the length of the lead to be protected, 10 percent would be about the minimum.

Alternatively, the portion of the lead that is protected from crushing could be anywhere from about 8 to about 18 centimeters in length. A more likely range would be from about 8 to about 12 centimeters in length though. We could also place the protected portion of the lead anywhere from 20 to 30 centimeters away from the distal tip of the lead, but as shown above, a preferred spacing is 25.3 centimeters away from the distal tip.

Of course, this all assumes that the lead is intended for implantation in the ventricle. If the lead is meant for use in either the right atrium or right ventricle, then we must allow for the shorter distance from the tip of the lead to the area of compression if the lead is implanted in the right atrium. Typically, the distance to the point of compression is 6 centimeters closer to the tip of a lead when a lead is implanted in the right atrium than when it is implanted in the right ventricle. Thus for leads that can be used in either the right atrium or right ventricle, the area to be protected from compression damage is preferably the portion extending from 19.3 centimeters to 35.7 centimeters proximal to the distal tip of the lead. The portion that is protected could reasonably be anywhere from 12 to 18 centimeters in length, but as described above, the protected portion is preferably 16.4 centimeters in length. The protected portion is preferably spaced 19.3 centimeters from the distal tip, but could be spaced away from the distal by about 15 to 25 centimeters.

Finally, for leads that are to be used only in the right atrium, we can see that the area of protection should the portion of the lead extending from 19.3 centimeters to 29.7 centimeters proximal to the distal tip of the lead. As with leads that are intended to be used only in the ventricle, we could conceivably protect a portion of the lead that is anywhere from about 8 to about 12 centimeters in length, but the preferred portion to be protected is 10.4 centimeters in length. The protected portion of the lead could be spaced away from the distal tip anywhere from about 15 to 25 centimeters, but the 19.3 centimeter spacing is the preferred one.

Figure 5:
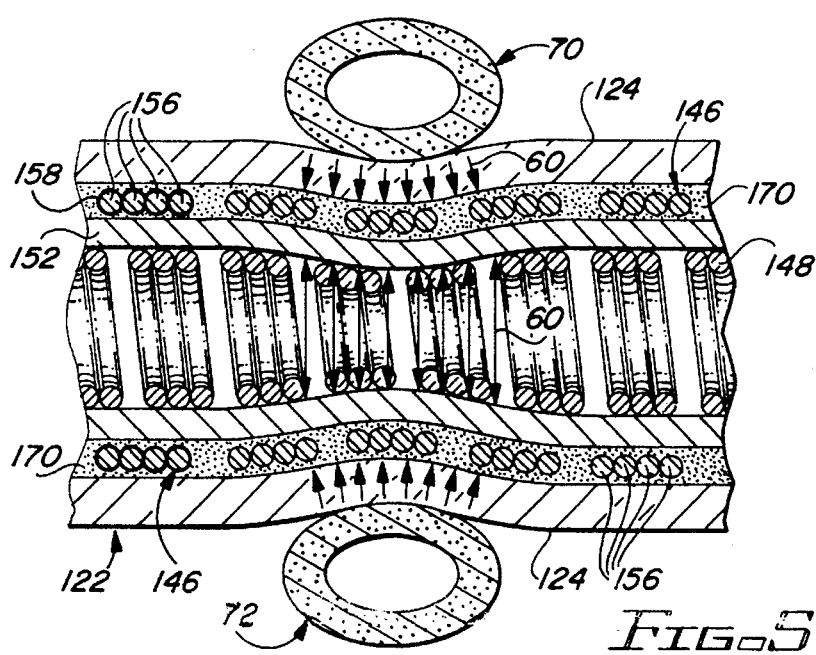
FIG. 5 shows a detailed partial cutaway axial view of a pacing lead according to the present invention in the area of the subclavian transition.
Figure 6:
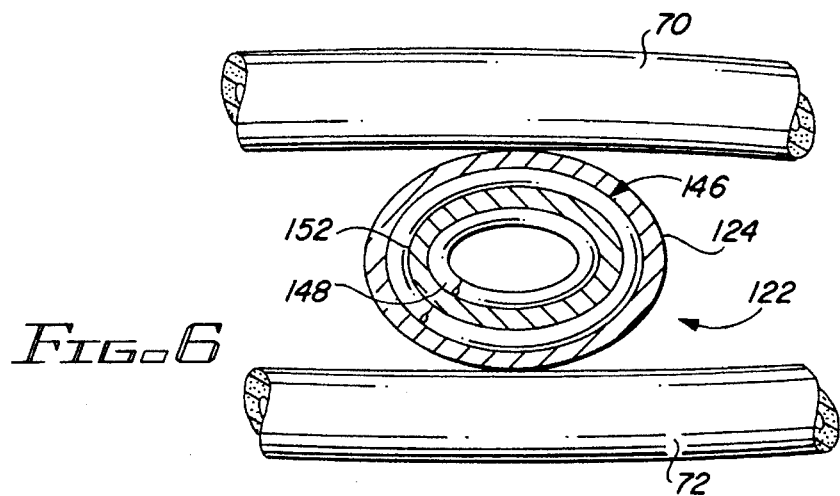
FIG. 6 shows a cross-sectional view of the pacing lead of the present invention in the area of the subclavian transition.

FIGS. 5 and 6 depict an axial and a cross-sectional view through portions of a lead body 122 of the present invention extending between the first rib 70 and clavicle 72, similar to the view of FIG. 4. It is to be understood that the conductors identified in FIGS. 4 and 6 appear solid in cross-section, which results from a tightly wound helix having many turns per inch. Obviously, for helixes with fewer turns per inch, the cross-section would show portions of adjacent windings. As shown in FIG. 5, the lead body 122 includes the insulation sheath 124 and insulation tubing 152 bounding the helical conductor 146. The helical conductor 146 may be made up of a plurality of conductors contained in a bundle 156 which are helically wound in a side-by-side manner. Each of the conductors contained in the bundle 156 may be individually coated or wrapped with an insulation material 158. In addition, a second conductor 148, which is also helically wound, is disposed internally of the insulation tubing 152.

As depicted in FIG. 5, a flexible insulative material 170, such as a silicone elastomer medical adhesive, has been interposed into the area bounded by the insulation sheath 124 and insulation tubing 152 to essentially encase the conductor 146 in the flexible insulative material 170. The flexible insulative material 170 thus coats and encapsulates the conductor 146 to the insulation tubings. The flexible insulative material 170 occupies the empty spacing between the insulation sheath 124 and insulation tubing 152.

The flexible insulative material 170 may be introduced in various ways, one of which could be by an injection process utilizing a syringe type of needle (not shown) which pierces the insulation sheath 124. The flexible insulative material is introduced while in a liquid state, and allowed to flow about the conductor 146. Following introduction, the flexible insulative material 170 solidifies, sealing the needle puncture of the insulation sheath 124. The flexible insulative material 170 increases the structural strength of the lead body 122 and, in particular, the conductor coil 146, and prevents localized bending, particularly sharp bending deformation, coil distortion, or compression of the conductor 146. The flexible insulative material 170 may be selected from the materials including silicone medical adhesive, silicone rubber, and polyurethane.

As illustrated in FIG. 5, the result of the inclusion of the flexible insulative material 170 is that the constriction forces applied by the first ribs 70 and clavicle 72 results in reduced distortion of the lead body 122, as compared to the construction illustrated in FIGS. 3 and 4. While the lead body 122 has enhanced structural stability, it still remains flexible due to the properties of the flexible insulative material which do not significantly impact the overall flexibility of the lead body 122.

The portion of the lead body 20 having the flexible insulative material 170 is as described above, and preferably covers a portion of the lead body 20 10.4 centimeters in length for those leads which are intended to be implanted in a particular heart chamber or 16.4 centimeters in length for those leads that may be positioned in either chamber. In the preferred embodiment, the diameter of the lead body is in the range of between about 1.50 mm and 3.50 mm and preferably about 2.5 mm.

Figure 7:
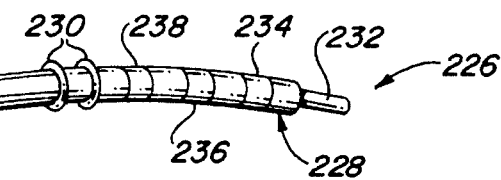
FIG. 7 shows a multilumen pacing lead.
Figure 7:
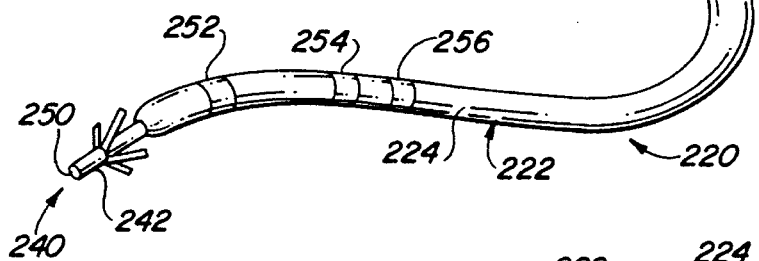

FIG. 7 shows an alternative embodiment depicting a multilumen pacing lead 220 according to the present invention. The multilumen pacing lead 220 has an elongated lead body 222 which includes electrical conductors extending through lumens within a multilumen tubing 224. The multilumen tubing 224 is preferably fabricated of silicon, rubber, polyurethane, or another suitable plastic material having the properties of biocompatibility, biostability and flexibility.

At a proximal end 226 of the pacing lead 220 is a connector assembly 228, which is provided with sealing rings 230 and which includes electrical connectors 232, 234, 236 and 238. The portions of the connector assembly 228 spacing apart the connectors 234, 236, and 238 may be fabricated from segments of multilumen tubing of silicone, rubber, polyurethane, or other suitable plastic, assembled in the manner discussed herein below. The electrical connectors 232, 234, 236 and 238 are preferably fabricated of stainless steel or other suitable conductive material.

At a distal end 240 of the pacing lead 220 is an electrode assembly 242. A tip electrode 250 is located at the distal end 240 of the electrode assembly 242. A number of ring electrodes 252, 254, and 256 are shown spaced proximally from the distal end 240 of the pacing lead 220. The ring electrode 252 may be used, for example, as a cathode in a bipolar pacing system. Alternatively, the electrodes 252, 254 and 256 can be used as sensor electrodes to determine various parameters of endocardial activity, such as atrial electrical activity, ventricular electrical activity, or to sense impedance changes to determine stroke volume, pre-ejection fraction, and respiratory rate. Monitoring of these parameters is beneficial for advanced pacing systems to allow the pacemaker to more effectively control the cardiac activity.

Figure 8:
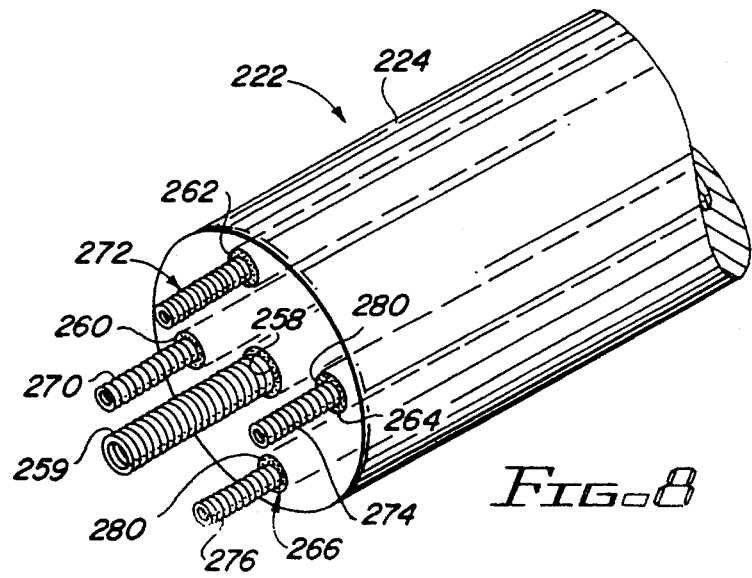
FIG. 8 depicts a partially cross-sectional perspective view of the multilumen pacing lead of FIG. 7 incorporating the present invention.

As shown in FIG. 8, the multilumen tubing 224 has a generally cylindrical cross-section with a central axial lumen 258 for receiving the conductor coil 259, and four lumens 260, 262, 264 and 266, which are spaced apart and axially aligned to extend along the length of the multilumen tubing 224. The lumens 260, 262, 264 and 266 provide enclosed pathways for electrical conductors 270, 272, 274 and 276. The electrical conductors 270, 272, 274 and 276 are preferably helical coils which, when inserted through the respective lumens 260, 262, 264, 266, each define an internal chamber or passageway.

Each of the lumens 260, 262, 264 and 266 is filled with a flexible material 280. This flexible material 280 is the same material as described above for FIGS. 5 and 6. The flexible material 280 may be introduced after the multilumen lead 220 has been assembled, for example by injection with a needle, or it can be introduced during assembly of the lead body 222. The flexible material minimizes the helical conductors 270, 272, 274 and 276 from being damaged by filling the internal chamber or passageway within each conductor 270, 272, 274 and 276.

It should be evident from the foregoing description that the present invention provides advantages over pacing leads of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. A pacemaker lead for use with a pacemaker adapted to receive an end of said pacemaker lead therein to form a pacing system, said pacemaker lead having a proximal end and a distal end, said pacemaker lead comprising:

a connector for insertion into the pacemaker to electrically connect said pacemaker lead to the pacemaker, said connector being located at said proximal end of said pacemaker lead;

a first electrode located at said distal end of said pacemaker lead;

an outer insulation tubing having a first lumen extending therethrough;

a first electrical conductor electrically connecting said connector to said first electrode, said first electrical conductor extending through said first lumen of said outer insulation tubing; and a first structural support means for inhibiting crushing of said first electrical conductor by external forces placed on said pacemaker lead, said structural support means being disposed within a portion of said first lumen of said outer insulation tubing extending between about ten percent and about thirty-five percent of the length of said pacemaker lead and surrounding a corresponding portion of said first electrical conductor, said structural support means being spaced away from said distal end of said pacemaker lead.

2. The pacemaker lead of claim 1, wherein said outer insulation tubing has a second lumen and said connector is a multipolar connector, said pacemaker lead further comprising:

a second electrode located at said distal end of said pacemaker lead; and a second electrical conductor electrically connecting said connector to said second electrode, said second electrical conductor extending through said second lumen of said outer insulation tubing.

3. The pacemaker lead of claim 2, further comprising:

a second structural support means for inhibiting crushing of said second electrical conductor by external forces placed on said pacemaker lead, said second structural support means being disposed within a portion of said second lumen of said outer insulation tubing extending not less than ten percent of the length of said pacemaker lead and surrounding a corresponding portion of said second electrical conductor, said second structural support means being spaced away from said distal end of said pacemaker lead.

4. The pacemaker lead of claim 1, wherein said first structural support means comprises:

a flexible insulative material encapsulating said corresponding portion of said first electrical conductor within said first lumen of said outer insulation tubing.

5. The pacemaker lead of claim 4, wherein said flexible insulative material is selected from the group of materials consisting of silicone medical adhesive, silicone rubber, and polyurethane.

6. The pacemaker lead of claim 1, wherein said first electrical conductor is hollow, said pacemaker lead further comprising:

an inner insulation sheath disposed within said first electrical conductor, said inner insulation sheath and an inner surface of said first lumen of said outer insulation tubing together defining a passageway therebetween in which both said first electrical conductor and said first structural support means are disposed.

7. The pacemaker lead of claim 6, wherein said inner insulation sheath has a lumen extending therethrough, said pacemaker lead further comprising:

a second electrode located at said distal end of said pacemaker lead; and a second electrical conductor extending through said lumen of said inner insulation sheath, said second electrical conductor electrically connecting said second electrode and said connector.

8. The pacemaker lead of claim 7, wherein said first structural support means comprises:

a flexible insulative material encapsulating said first electrical conductor within said first lumen of said insulation tubing.

9. The pacemaker lead of claim 8, wherein said flexible insulative material is selected from the group of materials consisting of silicone medical adhesive, silicone rubber, and polyurethane.

10. A pacemaker lead for use with a pacemaker adapted to receive an end of said pacemaker lead therein to form a pacing system, said pacemaker lead having a proximal end and a distal end, said pacemaker lead comprising:

a connector for insertion into the pacemaker to electrically connect said pacemaker lead to the pacemaker, said connector being located at said proximal end of said pacemaker lead;

a first electrode located at said distal end of said pacemaker lead;

an outer insulation tubing having a first lumen extending therethrough;

a first electrical conductor electrically connecting said connector to said first electrode, said first electrical conductor extending through said first lumen of said outer insulation tubing; and a first structural support means for inhibiting crushing of said first electrical conductor by external forces placed on said pacemaker lead, said structural support means being disposed within a portion of said first lumen of said outer insulation tubing extending approximately 8 to 18 centimeters in length and surrounding a corresponding portion of said first electrical conductor, said structural support means being spaced away from said distal end of said pacemaker lead.

11. The pacemaker lead of claim 10, wherein said portion of said pacemaker lead wherein said first structural support means is approximately 8 to 12 centimeters in length.

12. The pacemaker lead of claim 11, wherein said portion of said pacemaker lead wherein said first structural support means is approximately 10.4 centimeters in length.

13. The pacemaker lead of claim 11, wherein said pacemaker lead is adapted for use in the right ventricle of a human heart, and wherein said first structural support means is spaced approximately 20 to 30 centimeters away from said distal end of said pacemaker lead.

14. The pacemaker lead of claim 13, wherein said first structural support means is spaced approximately 25.3 centimeters away from said distal end of said pacemaker lead.

15. The pacemaker lead of claim 11, wherein said pacemaker lead is adapted for use in the right atrium of a human heart, and wherein said first structural support means is spaced approximately 15 to 25 centimeters away from said distal end of said pacemaker lead.

16. The pacemaker lead of claim 15, wherein said first structural support means is spaced approximately 19.3 centimeters away from said distal end of said pacemaker lead.

17. The pacemaker lead of claim 10, wherein said pacemaker lead is adapted for use in either the right atrium or the right ventricle of a human heart, and wherein said portion of said pacemaker lead wherein said first structural support means is disposed is approximately 12 to 18 centimeters in length.

18. The pacemaker lead of claim 17, wherein said portion of said pacemaker lead wherein said first structural support means is disposed is approximately 16.4 centimeters in length.

19. The pacemaker lead of claim 17, wherein said first structural support means is spaced approximately 15 to 25 centimeters away from said distal end of said pacemaker lead.

20. The pacemaker lead of claim 19, wherein said first structural support means is spaced approximately 19.3 centimeters away from said distal end of said pacemaker lead.

21. A method of inhibiting crushing of an electrical conductor in a pacemaker lead having a lead body wherein said electrical conductor is protected within an outer insulation sheath extending between and interconnecting a connector at a proximal end of said pacemaker lead and an electrode at a distal end of said pacemaker lead, the method comprising:

a) assembling said pacemaker lead; by
  1) placing said electrical conductor within said outer insulation sheath;
  2) placing said connector at said proximal end of said lead;
  3) electrically connecting said connector to said electrical conductor;
  4) placing said electrode at said distal end of said pacemaker lead; and
  5) electrically connecting said electrode to said electrical conductor; and b) providing a means for structurally supporting a portion of said electrical conductor, said portion extending between about ten percent and about thirty-five percent of the length of said pacemaker lead and wherein said portion is spaced away from said distal end of said pacemaker lead, wherein said means for structurally supporting inhibits crushing of said electrical conductor by external forces placed on said pacemaker lead.

22. The method as claimed in claim 21, wherein said providing step comprises:

injecting a flexible insulative material into said outer insulation sheath, whereby said flexible insulative material surrounds said portion of said electrical conductor.

23. A method of inhibiting crushing of at least one of a plurality of electrical conductors in a pacemaker lead having a lead body wherein said electrical conductors are protected within respective ones of a plurality of lumens extending through an outer insulation tubing, said outer insulation tubing extending between and interconnecting a multipolar connector at a proximal end of said pacemaker lead and a plurality of electrodes at a distal end of said pacemaker lead, the method comprising:

a) assembling said pacemaker lead; by
  1) placing said plurality of electrical conductors within respective ones of said plurality of lumens of said outer insulation tubing;
  2) placing said multipolar connector at said proximal end of said lead;
  3) electrically connecting said multipolar connector to said plurality of electrical conductors;
  4) placing said plurality of electrodes at said distal end of said pacemaker lead; and
  5) electrically connecting said plurality of electrodes to respective ones of said plurality of electrical conductors; and b) providing a means for structurally supporting a portion of said at least one of said plurality of electrical conductors, said portion extending between about ten percent and about thirty-five percent of the length of said pacemaker lead and wherein said portion is spaced away from said distal end of said pacemaker lead, wherein said means for structurally supporting inhibits crushing of said at least one of said plurality of electrical conductors by external forces placed on said pacemaker lead.

24. The method as claimed in claim 23, wherein said providing step comprises:

injecting a flexible insulative material into said outer insulation tubing, whereby said flexible insulative material surrounds said portion of said at least one of said plurality of electrical conductors.

* * * * *